United States Patent [19]

Ohnishi

[11] Patent Number: 4,837,163
[45] Date of Patent: Jun. 6, 1989

[54] SIMPLE BLOOD TEST FOR DIAGNOSING MALIGNANT HYPERTHERMIA

[76] Inventor: Tsuyoshi Ohnishi, 502 King of Prussia Rd., Radnor, Pa. 19087

[21] Appl. No.: 104,463

[22] Filed: Oct. 2, 1987

[51] Int. Cl.$^4$ .............................................. G01N 33/48
[52] U.S. Cl. ...................................... 436/63; 436/805; 436/811
[58] Field of Search ...................... 436/63, 92, 98, 161, 436/524, 525, 527, 529, 531, 532, 805, 811; 422/58–61; 435/7.17, 194, 815; 424/2, 12, 1.1, 9; 128/736, 369, 399, 402, 207.15, 303.1, 203.22; 568/449, 471; 548/309; 514/390

[56] References Cited

U.S. PATENT DOCUMENTS

| | | | |
|---|---|---|---|
| 4,260,678 | 4/1981 | Lepp et al. | 435/17 |
| 4,362,645 | 12/1982 | Hof et al. | 422/57 |
| 4,543,359 | 9/1985 | Ellis et al. | 548/309 |
| 4,600,696 | 7/1986 | Solomons | 436/63 |

OTHER PUBLICATIONS

"Calcium-Induced Ca$^{+2}$ Release from Sarcoplasmic Reticulum of Pigs Susceptible to Malignant Hyperthermia", Ohnishi et al., *FEBS*, 0771, 9–1983, vol. 163, No. 1, pp. 103–107.
"Abnormal Membrane Properties of the Sarcoplasmic Reticulum of Pigs Susceptible to Malignant Hyperthermia", Ohnishi et al., *Archives of Biochem. and Biophysics,* vol. 247, 6–1986, pp. 294–301.
"Effects of Halothane, Caffeine, Dantrolene, and Tetracaine on the Calcium Permeability of Skeletal Sarcoplasmic Reticulum of Malignant Hyperthermic Pigs", Ohnishi, *Biochimica et Biophisica Acta,* 897, pp. 261–268.

*Primary Examiner*—Barry S. Richman
*Assistant Examiner*—T. J. Wallen
*Attorney, Agent, or Firm*—Caesar, Rivise, Bernstein, Cohen & Pokotilow, Ltd.

[57] ABSTRACT

The invention provides a simple, non-invasive method of screening malignant hyperthermia using a few milliliters of blood drawn from an individual into an acid-citrate anti-coagulant. When blood preservation is not needed, the blood specimen is stored for several hours at room temperature, after which a small amount of blood is taken into a cuvette with the optical path of 0.1 mm. Then, by measuring optical densities at wavelengths of 542 and 578 nm, the susceptibility for malignant hyperthermia can be determined. When a blood specimen has to be shipped to a distant screening center, the specimen can be stored in a styroform container at 0°–4° C. with either wet ice or artificial coolant and delivered by an express carrier service. Upon arrival, optical measurement is done in a similar fashion.

3 Claims, 3 Drawing Sheets

SIMPLE BLOOD TEST FOR DIAGNOSING MALIGNANT HYPERTHERMIA

BACKGROUND OF THE INVENTION

1. Field of the Invention

The present invention relates to a new method of diagnosing malignant hyperthermia (MH) using a few milliliters of blood.

2. Background Art

MH is a serious complication of anesthesia with a high risk of death. The symptom (muscle rigidity and/or fever) is manifested when a genetically MH-susceptible individual receives general anesthesia or succinylcholine (a commonly used muscle relaxant) in the operating room. Currently, the only reliable method of screening this disorder is to surgically remove a piece of muscle from the suspect, and perform an elaborate laboratory test to investigate the effect of halothane (sometimes in conjunction with succinylcholine or caffeine) on the contractility of excised muscle fibers. This is such a stressful test for the suspect that many of possible patients (family members and blood-related relatives of a MH patient) do not want to take the test.

MH is observed in both human and pig. Isolating sarcoplasmic reticulum from skeletal muscle of genetically MH-susceptible pigs, the inventor pioneered to find functional structural abnormalities in the membranes of the sarcoplasmic reticulum.

(i) Functional: The sarcoplasmic reticulum of susceptible pigs is abnormally permeable to calcium, and halothane greatly enhances the calcium release from the sacroplasmic reticulum.

(ii) Structural: Halothane greatly fluidizes the membrane structure of the sarcoplasma reticulum. (See Ohnishi et al, FEBS LETTERS, Vol. 161, No. 1, September, 1983, pages 103–107; Ohnishi et al, Archiv. Biophys. Biochem., Vol. 247, No. 2, June, 1986, pages 294–301; and Ohnishi, Biochim. Biophys. Acta, Vol. 897, No. 2, February, 1987, pages 261–268.)

Using blood drawn from both MH-positive pigs and MH-positive patients, the inventor found that membranes of red blood cells have structural abnormality similar to that found in the sarcoplasmic reticulum. This is the basis that both sarcoplasmic reticulum and red blood cells may be regulated by the same gene, and that this genetic defect of skeletal muscle could be diagnosed by using red blood cells.

SUMMARY OF THE INVENTION

Currently, the only reliable screening method for MH is to perform muscle biopsy, which is not only a laborious procedure for the investigators, but also a painful test for suspected individuals. The present invention provides an alternative method, in which a few milliliters of blood is used to detect genetic disorders in the muscle. Stored blood can also be used for this method. Since blood is easily collected, this test could be done before surgery, thus enabling the suspect to receive a safe regimen of anesthesia. This test eliminates hesitation of the suspects toward the test, and contributes to a decrease of life-threatening mishaps in the operating room.

DETAILED DESCRIPTION OF THE INVENTION

An example of the method is set forth below. However, it is to be understood that this example is given by way of illustration only and is not to be construed as limiting the invention either in spirit or in scope, as many modifications both in composition of reagents and methods could be possible to those skilled in the art.

BLOOD COLLECTION AND PRESERVATION

Approximately 4 ml blood is collected in a 5 ml blue-top vacutainer containing acid citrate as an anti-coagulant. The vacuum is broken immediately after blood collection by puncturing the rubber cap by a needle for about 10 seconds. An alternative method is to collect 4 ml blood in a 5 ml green-top vacutainer containing heparine as an anti-coagulant. Then, vacuum is broken as described above, 0.6 ml blood-bank preservative (citrate-phosphate-dextrose-adenine) is added and mixed gently with the blood.

These blood specimens can be preserved in wet ice or with artificial coolant for several days. When preservation is not needed, blood can be kept at room temperature for several hours. Two examples are described below.

Example 1. Measurement without preservation

Figure 1:
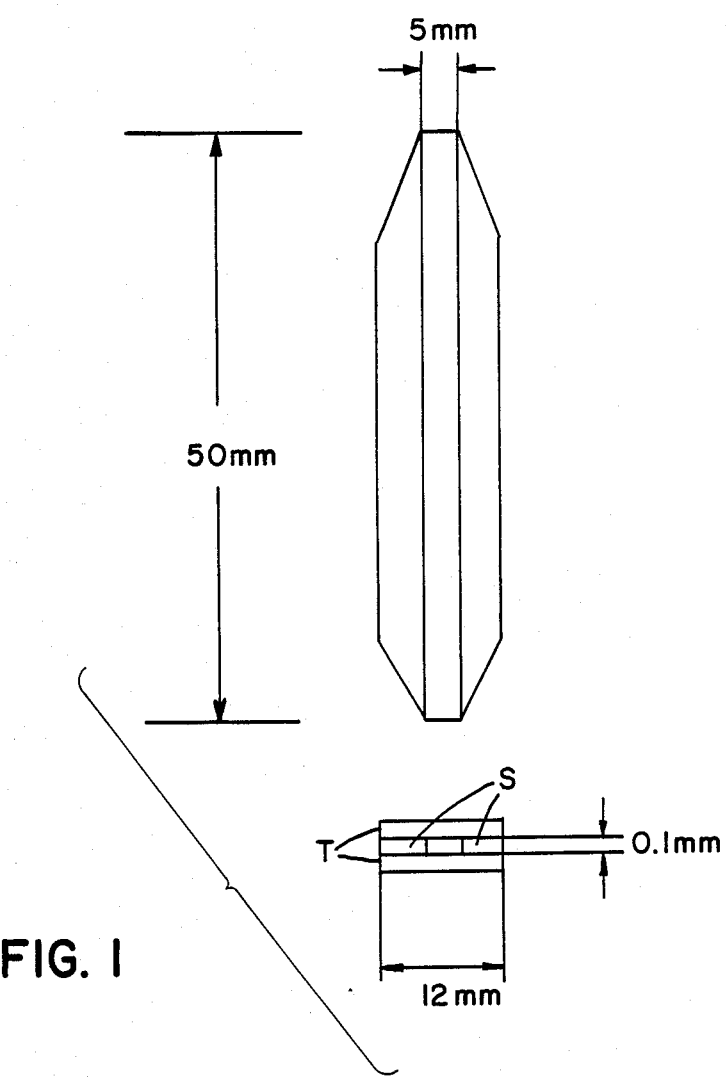
Figure 2B:
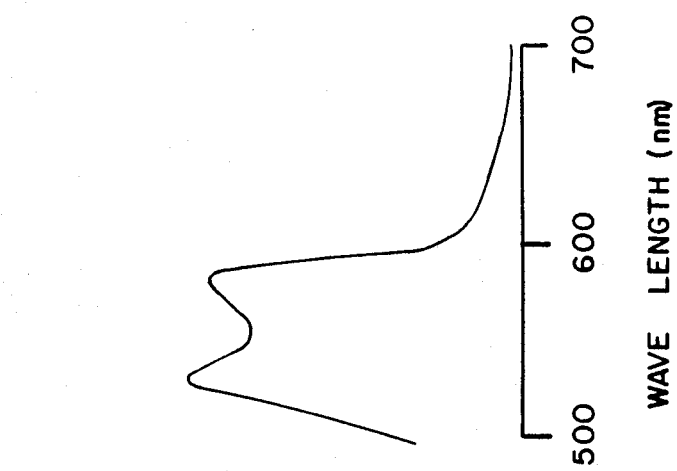
Figure 2A:
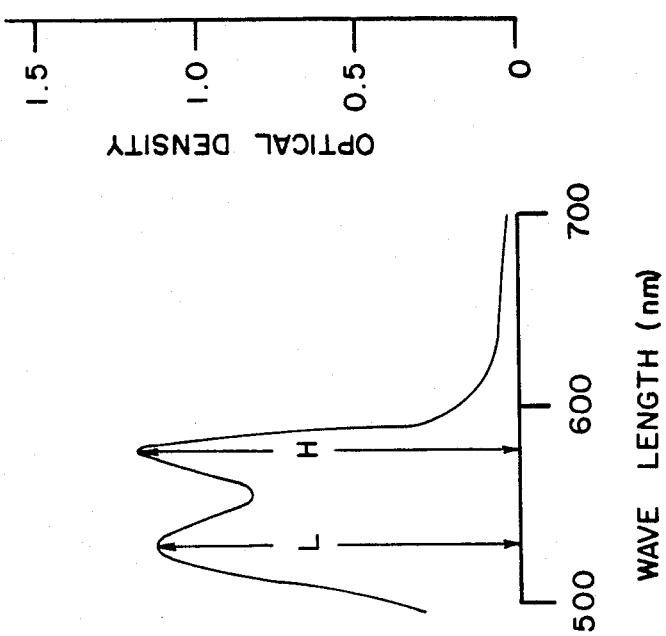

After several hours of storage at room temperature (20°–25° C.), blood is gently transfered into a special cuvette which has an optical path of 0.1 mm (see FIG. 1). Both ends of the cuvette are sealed with a hematocrit-tube sealant. Then the cuvette is placed in a spectrophotometer and a wavelength scanning is made between 500 and 700 mm. As shown in FIG. 2B, with the blood drawn from MH-susceptible patients, the absorption peak at 542 nm was larger than that at 578 nm. On the contrary, with the blood drawn from MH-negative (normal) subject, the peak at 578 nm is higher than that at 542 nm (FIG. 2 A). The value of optical density at 542 nm is denoted as L and that at 578 nm is denoted as H. The index M is defined by $$M = (L - H)/H.$$

If M is positive, the patient is MH-positive, and if the value is negative, the patient is MH-negative.

Example 2. Measurement after preservation

Figure 3:
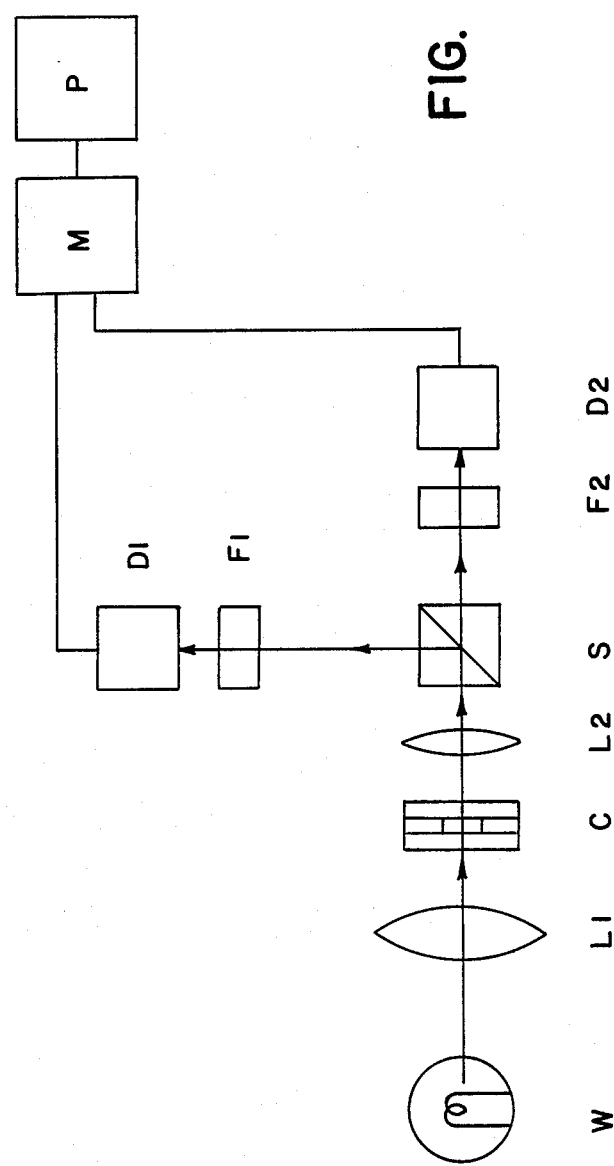

If the blood has to be shipped to a distant screening center, the blood is cooled with either wet ice or artificial coolant in a styrofoam box. The box is then shipped by express carrier service. Upon arrival, samples are gently transfered to the cuvette and measurement can be done at room temperature in the same way as described in Example 1. Again, if M is positive, the person is MH positive and if M is negative, the person is MH-negative. Example 3. Special instrumentation for this test The value of M could be detected without wavelength scanning. FIG. 3 shows the principle of this method. The cuvette is illuminated by a tungsten lamp with a proper oclimating device. Then, the light which passed the specimen was split into 2 beams with a beam splitter, and after leading through two optical filters (542 nm and 578 nm), the light intensities of both beams were detected by photo detectors. Then the signals are fed into a microprocessor and the optical densities are calculated. First, the intrument is standardized with water in the cuvette; the optical densities at both wavelength are defined as 0. Then the cuvette with blood specimen is inserted, and the optical densities at 542 and 578 nm are measured. The value M is calculated by a microprocessor and the result can be printed out. Two filters could be replaced by either a prism or a grating type monochrometer.

FIGURE LEGENDS

FIG. 1. Schematic illustration of a special cuvette with the optical path of 0.1 mm. T: transparent material, such as glass or plastic. S: opaque material made of glass or plastic which serves as a spacer. Blood fills the curvette by surface tension. After the cuvette was filled, both ends will be sealed by a hematocrit-tube sealant.

FIG. 2. Absorption spectra of blood specimens prepared from (A) normal individual and (B) malignant hyperthermia susceptible individual.

FIG. 3. Schematic illustration of a spectrophotometer with which diagnosis for malignant hyperthermia can be easily performed. W: Lamp; $L_1, L_2$: Lenses; C: Cuvette; $F_1$: 578 nm filter; $F_2$: 542 nm filter; $D_1, D_2$: Photodetectors and Amplifiers; M: Microprocessors; P: Printer.

What is claimed is:

1. A method of diagnosing susceptibility to malignant hyperthermia using unpreserved blood comprising drawing under a vacuum approximately 4 ml blood from an individual by venipuncture using a vacuum tube (citrate as an anti-coaggulant); breaking the vacuum of the vacuum tube by puncturing a rubber stopper of said vacuum tube by a syringe needle for about 10 seconds; gently transfering the blood after blood collection into an optical cuvette with a light path of 0.1 mm; measuring hemoglobin absorption using a scanning type spectrophotometer by scanning between 700 and 500 nm; measuring the absorption at 542 and 578 nm, and denoting them as L and H, respectively; calculating a value of M by equation $M=(L-H)/H$; diagnosing as malignant hyperthermia susceptible, if M is positive; and diagnosing as malignant hyperthermia negative, if M is negative.

2. A method of diagnosing susceptibility for malignant hyperthermia using a small amount of preserved blood comprising securing a sample of preserved blood, collecting the blood sample into a vacuum tube and breaking the vacuum by puncturing a rubber stopper of said vacuum tube by a syringe needle for about 10 seconds; storing the vacuum tube at 0°-4° C. for 1 to 5 days; taking out of storage the vacuum tube any time during storage, and measuring hemoglobin absorption by using a scanning type spectrophotometer by scanning between 700 and 500 nm; measuring the absorption at 542 and 578 nm, and denoting them as L and H, respectively; and calculating a value of M by equation $M=(L-H)/H$; and diagnosing the malignant hyperthermia susceptibility if M is positive; and diagnosing as malignant hyperthermia negative, if M is negative.

3. A method of collecting blood for the diagnostic method of claim 2 comprising using a heparine containing vacuum tube to draw 4 ml blood; adding 0.6 ml of citrate-phosphate-dextrose-adenine preservative; breaking the vacuum for about 10 seconds by a syringe needle.

* * * * *